United States Patent
Källstrand

(10) Patent No.: US 10,098,562 B2
(45) Date of Patent: Oct. 16, 2018

(54) SYSTEM AND METHOD FOR IMPROVED DETERMINATION OF A BRAIN RESPONSE STATE

(71) Applicant: Sensodetect AB, Lund (SE)

(72) Inventor: Johan Källstrand, Lund (SE)

(73) Assignee: SensoDetect AB, Lund (SE)

( * ) Notice: Subject to any disclaimer, the term of this patent is extended or adjusted under 35 U.S.C. 154(b) by 820 days.

(21) Appl. No.: 14/381,916

(22) PCT Filed: Mar. 5, 2013

(86) PCT No.: PCT/EP2013/054450
§ 371 (c)(1),
(2) Date: Aug. 28, 2014

(87) PCT Pub. No.: WO2013/131932
PCT Pub. Date: Sep. 12, 2013

(65) Prior Publication Data
US 2015/0073293 A1 Mar. 12, 2015

Related U.S. Application Data

(60) Provisional application No. 61/606,854, filed on Mar. 5, 2012.

(30) Foreign Application Priority Data

Mar. 5, 2012 (EP) ..................................... 12158150

(51) Int. Cl.
*A61B 5/0484* (2006.01)
*A61B 5/04* (2006.01)
(Continued)

(52) U.S. Cl.
CPC ...... *A61B 5/04845* (2013.01); *A61B 5/04012* (2013.01); *A61B 5/165* (2013.01); *A61B 5/4088* (2013.01); *A61B 5/4848* (2013.01)

(58) Field of Classification Search
CPC . A61B 5/04012; A61B 5/04845; A61B 5/165; A61B 5/4088; A61B 5/4848
(Continued)

(56) References Cited

U.S. PATENT DOCUMENTS

| | | | | |
|---|---|---|---|---|
| 4,188,956 A | * | 2/1980 | John | ..................... A61B 5/0424 600/544 |
| 4,201,224 A | * | 5/1980 | John | ..................... A61B 5/0476 600/544 |

(Continued)

OTHER PUBLICATIONS

WIPO, European International Preliminary Examining Authority, International Preliminary Report on Patentability dated Jun. 16, 2014 in International Patent Application No. PCT/EP2013/054450, 13 pages.

(Continued)

*Primary Examiner* — Navin Natnithithadha
(74) *Attorney, Agent, or Firm* — Inskeep IP Group, Inc.

(57) ABSTRACT

A device and a method for detecting a brain response state of a subject id disclosed. The detection comprises repeatedly presenting the subject with a sound stimulus for evoking a brain response. Detecting the evoked brain response signal related to each of said sound stimulus. Determining a window having a time width covering at least partly an area of at least one neuron's evoked response in the brain response signal. Calculating an average response signal over the window and comparing the at least one neuron's evoked response with the average response signal for determining a cellular variance and/or volatility.

18 Claims, 9 Drawing Sheets

(51) Int. Cl.
*A61B 5/16* (2006.01)
*A61B 5/00* (2006.01)

(58) Field of Classification Search
USPC .................................................. 600/544, 545
See application file for complete search history.

(56) References Cited

U.S. PATENT DOCUMENTS

| | | | | |
|---|---|---|---|---|
| 4,705,049 A * | 11/1987 | John | ................... | A61B 5/0484 600/544 |
| 5,699,808 A * | 12/1997 | John | ................... | A61B 5/0484 600/483 |
| 6,016,444 A * | 1/2000 | John | ................... | A61M 16/104 128/910 |
| 6,052,619 A * | 4/2000 | John | ................... | A61B 5/0476 600/544 |
| 6,196,977 B1 * | 3/2001 | Sininger | ............ | A61B 5/04845 600/545 |
| 6,200,273 B1 | 3/2001 | Sininger et al. | | |
| 6,385,486 B1 * | 5/2002 | John | ................... | A61B 5/0002 600/544 |
| 6,743,185 B2 | 6/2004 | Thornton | | |
| 7,471,978 B2 * | 12/2008 | John | ................... | A61B 5/0002 600/544 |
| 8,292,823 B2 * | 10/2012 | Olsson | ............... | A61B 5/04845 600/544 |
| 8,700,142 B2 * | 4/2014 | John | ................... | A61B 5/0002 600/544 |
| 2002/0091335 A1 * | 7/2002 | John | ................... | A61B 5/0002 600/544 |
| 2003/0185408 A1 | 10/2003 | Causevic et al. | | |
| 2007/0299359 A1 * | 12/2007 | Olsson | ............... | A61B 5/04845 600/544 |
| 2009/0076407 A1 * | 3/2009 | John | ................... | A61B 5/0002 600/544 |
| 2009/0220425 A1 | 9/2009 | Moxon et al. | | |
| 2009/0227889 A2 * | 9/2009 | John | ................... | A61B 5/0002 600/544 |
| 2013/0131536 A1 * | 5/2013 | Olsson | ............... | A61B 5/04845 600/544 |
| 2013/0231581 A1 * | 9/2013 | Kallstrand | ......... | A61B 5/04845 600/544 |

OTHER PUBLICATIONS

WIPO, European International Search Authority, International Search Report dated May 24, 2013 in International Patent Application No. PCT/EP2013/054450, 3 pages.

* cited by examiner

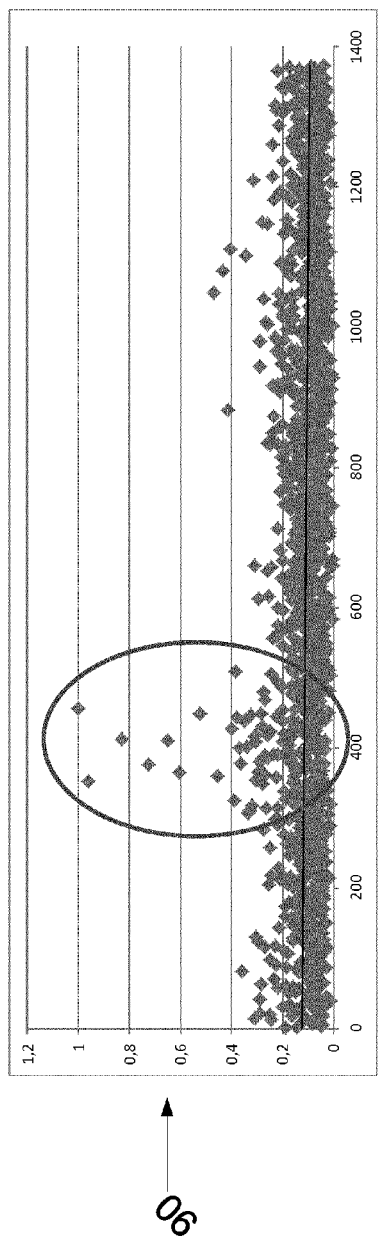
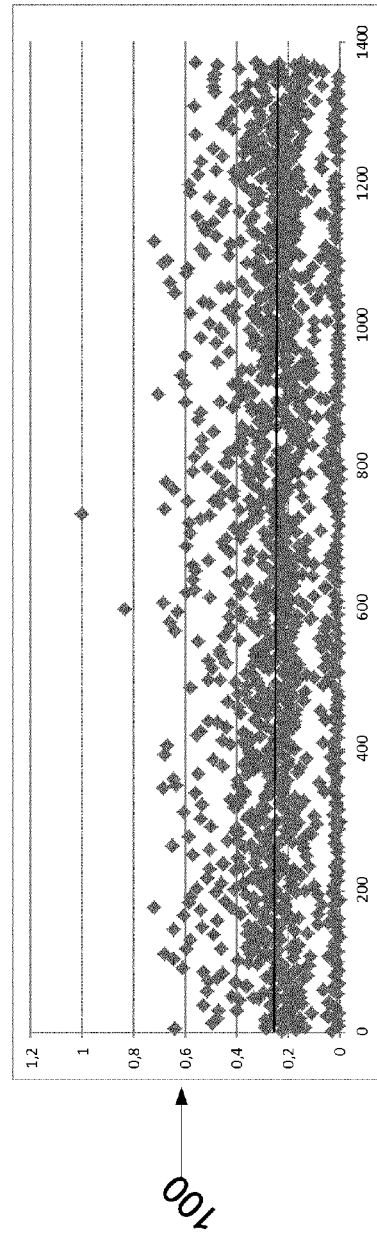
Fig. 7A
Fig. 7B

SYSTEM AND METHOD FOR IMPROVED DETERMINATION OF A BRAIN RESPONSE STATE

RELATED APPLICATIONS

This application is the U.S. National Phase of and claims priority to International Patent Application No. PCT/EP2013/054450, International Filing Date Mar. 5, 2013, entitled System And Method For Improved Determination Of A Brain Response State, which claims benefit of European Patent Application No. 12158150.8, filed Mar. 5, 2012 entitled System And Method For Improved Determination Of A Brain Response State; and U.S. provisional application Ser. No. 61/606,854, filed Mar. 5, 2012entitled System And Method For Improved Determination Of A Brain Response State; all of which are incorporated herein by reference in their entireties.

BACKGROUND OF THE INVENTION

Field of the Invention

This invention pertains in general to the field of stimulatory, particularly auditory brain response, and related devices, systems and methods. More particularly the invention relates to an improved system and method for analysing the brain response development and more particularly the invention relates to an improved determination of brainstem response development.

Description of the Prior Art

It is known that auditory brainstem response audiometry can be used for screening test to monitor for hearing loss or deafness. If using complex sound stimuli auditory brainstem response can be used to assess brain stem disorders using sound stimuli. When auditory brainstem methods are used for diagnosis of brainstem disorders they rely on data set of normal healthy subjects for comparisons as a step in the assessments. The assessments may also be time consuming and in most cases can not be performed in real-time. Real-time analysis can be an important tool when evaluating brainstem response state development, such as the affected by certain stimuli, such as psychoactive compounds or substances including psychopharmaceuticals, alcohol, drugs but also therapeutic treatments.

In US 2009/0220426 a method for evaluating an effect of a psychotropic compound or a treatment on a neuronal activity of an animal including determining a change in the amount of information generated by neurons in response to at least one repeatedly applied stimulus. Also provided is a method of screening psychotropic compounds for effectiveness on an animal which involves using a change in sensory discrimination in a population of neurons of the animal, wherein the sensory discrimination is obtained in response to one or more stimuli repeatedly applied to the animal.

The signals were recorded by utilizing surgically implanted arrays of electrodes. All disclosed tests relate to somatosensory and especially investigations of spatial and temporal structure of the receptive field by touching different locations. Even though auditory stimuli is mentioned in the description, it is not disclosed how to use sound stimulus to carry out these investigations.

Post-stimulus time histogram (PSTH) is typically not used in humans. It cannot be applied to determine stimulus induced activity in several parts of the brain simultaneously, as it demands recording of a certain chosen structure. Thus the PSTH is suited for animal research when the researcher knows what part of the brain to look in, but is not a good choice when the researcher wants to see what parts of the brain reacts in relation to a psychoactive compound.

Thus a technique aiming at giving guidance for the researcher, not only the amplitude of the psychoactive drugs effect, but also where it affects the brainstem would be an advantage. It is wanted to compare different parts of the brainstem, without having to position the device in specific neurons, as is the typical case with PSTH.

Hence, an improved device, and a method thereof, for diagnosis of brainstem disorders and/or the influence of a psychoactive compounds or substances on a subject, would be advantageous and in particular a device allowing for a testing procedure that does not rely on any cognitive effort from the subject would be advantageous. Also, improved specificity and reliability of the diagnosis should be more advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device and a method, according to the appended patent claims.

An evoked response state of a subject is determined over a number of evoked responses as a function of cellular variance and/or volatility. More particularly the disclosure provides obtaining a complex profile of cellular uncertainties in the evoked responses. The sound stimuli is here auditory stimuli which may be referred to as "sound pulses", but can in some examples be transient peaks, clicks, tone bursts, or other suitable types of auditory stimuli suitable for repetitive presentation.

According to aspects of the disclosure, a method is provided for detecting a brain response state of a subject by determining cellular variance and/or volatility of at least one neuron's evoked response. This is performed by:

Repeatedly presenting the subject with a sound stimulus for evoking a brain response.

Detecting the evoked brain response signal related to each of the sound stimulus.

Determining a window having a time width covering at least partly an area of the at least one neuron's evoked response in the brain response signal.

Calculating an average response signal over the window.

Comparing the at least one neuron's evoked response with the average response signal for determining a cellular variance and/or volatility.

The term "one neuron" or "a group of neurons" refers herein to a neuron or a group of neurons belonging to the same cluster or structure, such as a nucleolus, interconnected nuclei or a layer. An evoked response from this one neuron or group of neurons may form a peak on a recorded response signal. If no response is evoked no peak may be formed related to this one neuron or group of neurons.

The brain response is preferably the evoked brainstem response. The response signal from the brain stem is obtained 0 to 10 ms after presenting the subject with a sound stimulus.

In some examples of the disclosure of the method, the cellular variance and/or volatility is determined based on difference in amplitude.

In some further examples of the method, the cellular variance and/or volatility is determined based on difference in latency.

In some further examples of the method, calculating the average is based on a number of response signals.

The variance for an evoked response may also be calculated using only an average calculated from the same evoked response within the window. Subparts of the evoked response is then compared to this calculated average. This may be used to estimate swing or shift in the selected evoked response area.

In some further examples of the method, the method is used for determining a brain disorder, such as a brain stem disorder.

In some further examples of the method, the method is used for detecting an effect of a substance or compound on the brain of a subject.

In some further examples of the method, the effect is detectable in real-time. The may be important when evaluating or assessing the effect of a psychoactive compounds or substances on a subject.

According to another aspect of the disclosure, a device is provided, for detecting a brain response state of a subject by determining cellular variance and/or volatility of at least one neuron's evoked response. The device comprises a sound stimuli generating unit operative to repeatedly present the subject with a sound stimulus for evoking a brain response. The device further comprises a detection unit operative to detect the evoked brain response signal related to each of the sound stimulus and a storage unit operative to store information based on evoked brain response signal. Further the device comprises a control unit for determining a window having a time width covering at least partly an area of the at least one neuron's evoked response, and for calculating an average response signal over the window, and for comparing the at least one neuron's evoked response with the average response signal for determining a cellular variance and/or volatility.

In some examples of the device, the cellular variance and/or volatility is determined based on difference in amplitude of the area.

In some further examples of the device, the cellular variance and/or volatility is determined based on difference in latency of the area.

In some further examples of the device, the brain response is a brainstem response.

In some further examples of the device, the cellular variance and/or volatility is used for determining a brain disorder; and/or an effect of a substance or compound on the brain of a subject.

According to another aspect of the disclosure, computer-readable medium having embodied thereon a computer program for processing by a computer, for detecting a brain response state of a subject by determining cellular variance and/or volatility of at least one neuron's evoked response. The computer program comprises code segments for:

Repeatedly presenting the subject with a sound stimulus for evoking a brain response.

Detecting the evoked brain response signal related to each of the sound stimulus.

Determining a window having a time width covering at least partly an area of the at least one neuron's evoked response in the brain response signal.

Calculating an average response signal over the window.

Comparing the at least one neuron's evoked response with the average response signal for determining a cellular variance and/or volatility.

The computer program may be executed on a computer or micro-processor, such as being part of a control unit.

Auditory stimuli may be defined or referred to as "sound pulses" or signals, including but not limited to, transient peaks, clicks, tone bursts, or other suitable types of auditory stimuli suitable for repetitive presentation. The stimuli should be auditory perceptive to the subject to whom the stimuli is presented. Thus as defined within the area of psychoacoustics the sound stimuli presented to a human subject may have any frequencies between 20 Hz and 20000 Hz, and the amplitude may be from the lower limit of audibility defined as 0 dB or higher but preferably below damaging level for the frequencies used. Preferably may be to use an amplitude being a minimum threshold amplitude or higher for the particular frequencies used, but below damaging level for the frequencies. Preferably the amplitude may be between about 0 to 120 dB, preferably between about 0 to 100 dB, preferably between about 0 to 90 dB, preferably about 70 dB.

The time width or duration of each sound pulse may be in the range of 0.1 to 1000 ms. Preferably the time with or duration of each sound pulse may be approximately the time of the detection of the evoked response of the brainstem, thus preferably between 0 to 100 ms, such as 0 to 50 ms, such as 0 to 10 ms.

The detectable cellular variance and/or volatility of evoked brainstem response may be used to detect the effect pharmaceutical drugs/medicament may have on a subject for treatment, ease or relive of a disorder and/or disease. Wherein the subject could suffer from for example brainstem disorders; disorders of the nervous system or on neural states or other form of diseases or disorders having detectable lateral brainstem response states. Examples, but not limited to, may be drugs related to: ADHD, depression, anxiety, bipolar disorder, schizophrenia, Asperger syndrome, epilepsy, stress, relaxation, pain, immune response, allostasis; hypnotic, analgesia or similar.

A psychoactive, chemical or herbal compound or substances may refer to different types of drugs such as medical drugs, psychoactive drugs, psychopharmaceutical, psychotropic, anesthesia, pain controllers, psychiatric medication, illicit drugs, drugs of abuse and drugs associated thereof. Compound or substances may refer to compound or substances have an influence on a subject or patient's central nervous system or may affect the brain functioning resulting in changes in perception, mood, consciousness, cognition or behavior.

Therapy may herein refer using a drug or counseling, such as different kind of psychotherapy, for to treatment of a diagnosis or ease of symptoms but may also refer to drug or counseling for preventive therapy or supportive therapy.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which

FIGS. 7A and 7B are illustrating an example of measurements performed on one reference subject (FIG. 7A) and one subject diagnosed with ADHD (FIG. 7B), the selected area of the response signal is the thalamus area;

DESCRIPTION OF THE PREFERRED EXAMPLES

Figure 1:
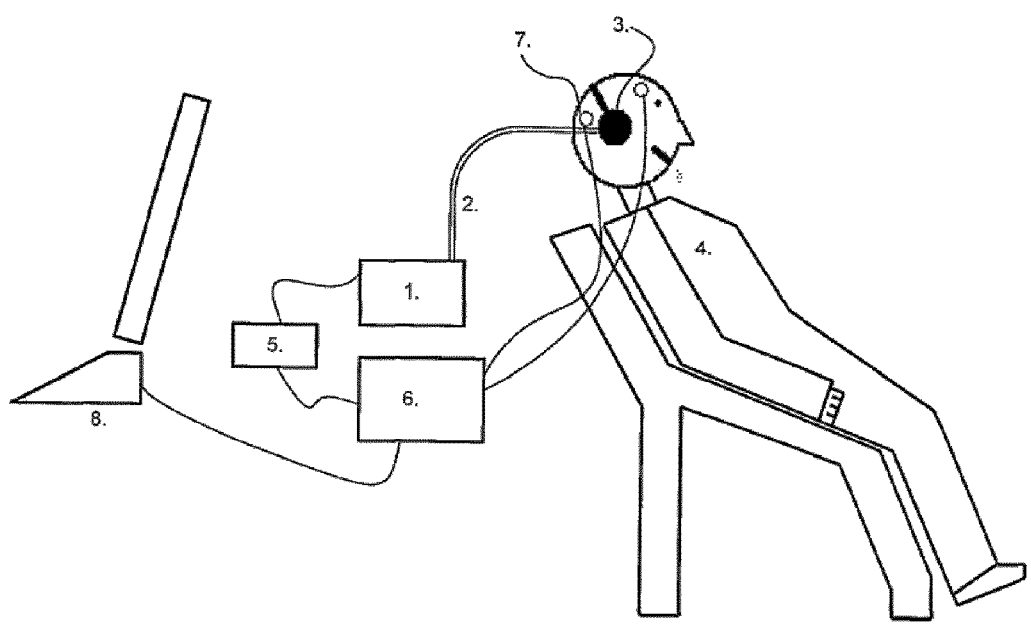
FIG. 1 is illustrating a schematic illustration of a device according to one example of the present disclosure.

Specific examples of the disclosure now will be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The terminology used in the detailed description of the examples illustrated in the accompanying drawings is not intended to be limiting of the disclosure. In the drawings, like numbers refer to like elements.

The present disclosure uses according to some examples auditory brainstem response (ABR) to detect brain disorders, such as brainstem disorder or disorders of the nervous system or on neural states or other form of diseases or disorders having detectable brainstem response states. It may also be used to detect a brainstem response state development for establishing an effect of a psychoactive compound, substance, food or pharmaceutical drugs/medicament.

The term "auditory brainstem response" is commonly used to define electrophysiological measurement of the activity of the brainstem within a time span of 0 to approximately 10 ms. Of course this time span may vary somewhat, but not principally deviate from this time span, while still be inside the scope of the present disclosure, according to the appended claims.

FIG. 1 is illustrating an exemplary device according to the present disclosure. The device comprises a sound stimuli generating unit 1, such as a tone generator, for repeatedly generating and sending a sound stimulus. The generated sound stimulus is being presented via a communication element 2 to a sound transmitting device 3, such as a hearing phone, to a subject 4.

Simultaneously as the sound stimulus is being presented, a trig-pulse is transmitted from the sound stimuli generating unit 1 to a triggering device (5), such as a trig-box, and further on to a storage unit for storage of information 6, such as brainstem activity, in which registration of electrophysiological brain activity from the detection unit 7, such as electrodes, is initiated. Hereafter the activity is imaged and analyzed on a control unit 8, such as a computer equipment. The triggering of registration is hence initiated by each start of a stimulus. The analyzing performed by the control unit 8 may be conducted according to the principles disclosed hereinafter.

The electrodes used to detect the brainstem signals are positioned on the head of the subject. Preferably, the electrodes are detachable attached to the skin of the subject's head. For example, the electrodes may be attached at the mastoid bone, the forehead and behind the ears. Other positions may be possible as well depending on the signals to be detected and recorded.

Common features for the tests used are that the sound stimuli is being presented to the subject in repeated sequences; typically sound stimuli are repeated approximately 500-1500 times. A complete test with high reliability is provided that takes only some minutes. Because of the fact that each stimulus is registered when the trig-pulse initiates the imaging apparatus, the brain activity caused by the stimulation appears more significantly on a continuous basis in relation to other brainstem activity. In this way the brainstems specific responses to stimuli are registered.

Alternatively, in some examples of the disclosure, the sound stimulus may comprise a first train of sound pulses and at least a second consecutive train of the same sounds pulses but modified. The first train of sound pulses may evoke a first response signal as a response to the first train of unmodified sound pulses. The second train of modified sound pulses may evoke a second response signal as a response to the second train of modified sound pulses. The response signal from the second train is compared to the response signal of the first train for each stimulus. Thus the test subject is his own reference and problems associated with absolute values may be avoided. The method is disclosed in PCT/EP2011/065340 of the same applicant as the present application which is incorporated by reference herein in its entirety for all purposes. Using a stimulus comprising a first train of unmodified sound pulses followed by a consecutive second train of modified sound pulses adds an extra dimension, by correlation of the subject's brain activity alteration, to the specific sound modification.

Figure 2:
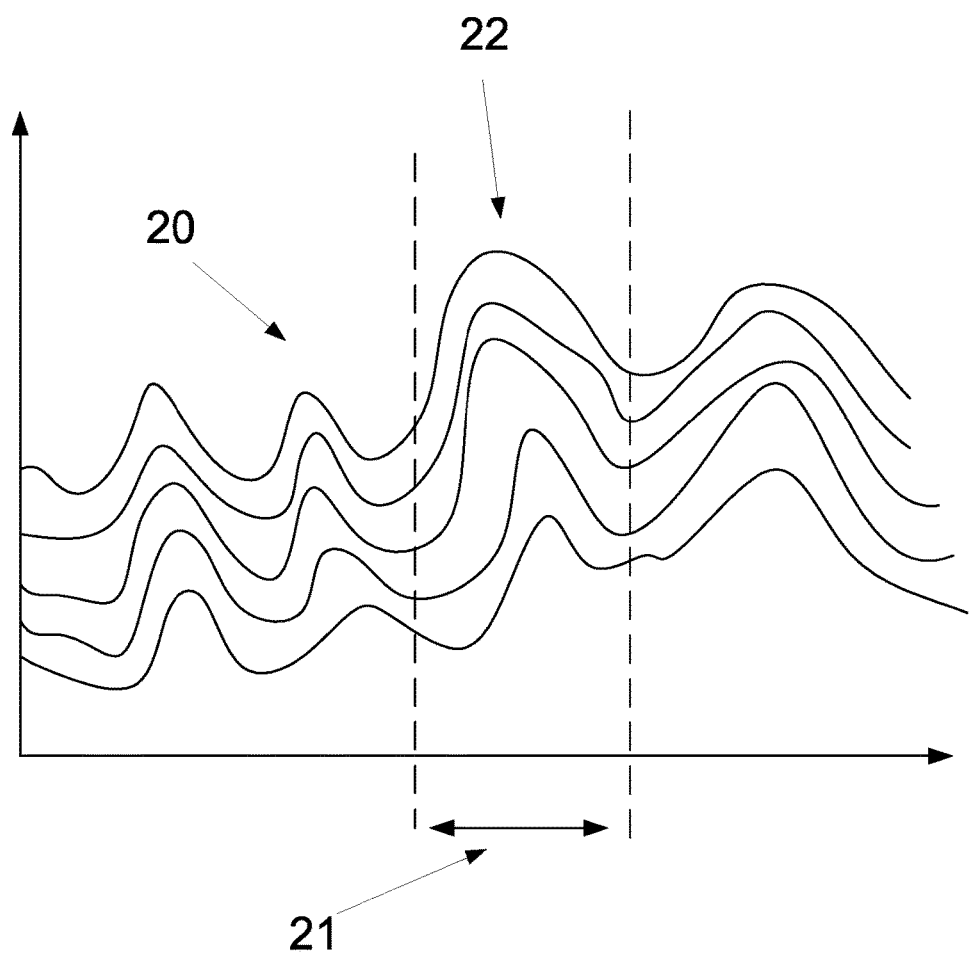
FIG. 2 is illustrating a brainstem response audiograms over the time range 0 and 10 ms.

FIG. 2, is illustrating brainstem response audiograms 20 over the time range 0 and 10 ms. Each curve is illustrating a response to a single stimulus. The peaks of the curves illustrate different areas of one neuron's evoked response or a group of neurons' evoked response to the presented stimuli. There are about thirteen different sound stimuli, such as pulses or clicks, known to evoke a brainstem response. In WO 2006/062480, of the same applicant as the present application which is incorporated by reference herein in its entirety for all purposes, such sound pulses are described in more details.

The dashed lines are illustrating a window 21 having a width in time. The window 21 has an area 22 covering at least partly at least one neuron's evoked response, such as a group of neurons' evoked response. In the illustration, a window with a time width 21 has been selected to cover one of the at least one neuron's evoked response.

Additionally, for determining the variance and/or volatility for more than one cluster or structure of at least one neuron's evoked response, each at least one neuron's evoked response, belonging to the same cluster or structure, may have their own determined window with a time width 21.

For evaluation of normal auditory brainstem responses, all curves are used to obtain an average curve. Only this average curve is then being used for detection of for example a disorder. For the disclosure herein, as will be presented, information from each evoked response curve is used individually to obtain more data and information. This may increase the likelihood to obtain a higher degree of security in providing the right diagnosis. It may also make it possible to obtain the results of a test faster. It may also expand the usability of ABR to other areas such as real-time analysis of a subject's response to psychoactive, chemical or herbal compound or substances.

Figure 3A:
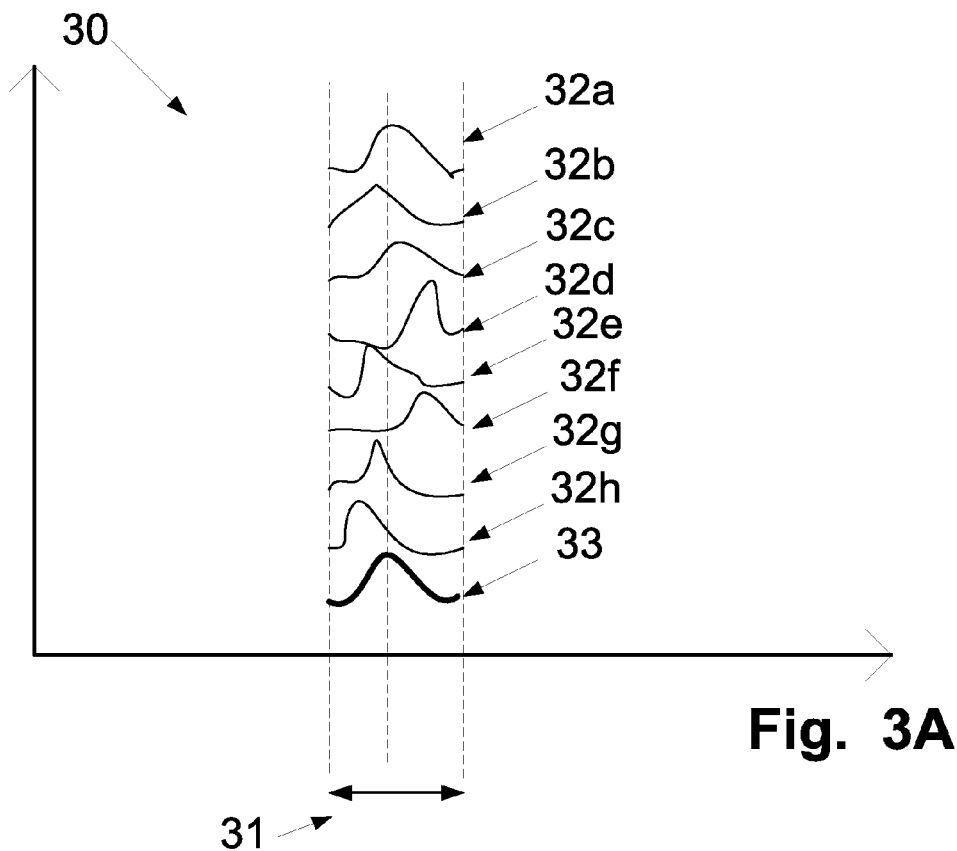
FIG. 3A is illustrating a graph for illustrating a principle of determining cellular latency variance and/or volatility of one neuron's evoked response in a window having a time width.

FIG. 3A, shows a graph 30 for illustrating a principle of determining cellular latency variance and/or volatility of at least one neuron's evoked response, such a the evoked response from a group of neurons, in a window having a time width 31. The width of the window may be in the range 1 to 4 ms, preferably around 2 to 3 ms, such as about 2.5 ms. The width has to be large enough to cover a sufficient area of a selected at least one neuron's evoked response but not so large that it may overlap an area of a neighbouring neurons' evoked responses. The cellular latency variance and/or volatility are a measure of uncertainty in the selected neuron cells. Peak 33 illustrates a determined average latency from a number of evoked responses of at least one neuron, such as a group of neurons belonging to the same cluster or structure. By comparing the latency of each peak 32a-32h with the latency of the average evoked response of peak 33, the variance and/or volatility for each evoked response of at least one neuron may be calculated with respect to latency. The average latency may be calculated by using all the evoked responses from a series of repeated sound stimulus.

Alternatively, for example when doing real-time evaluations, the average latency may be calculated from a first subseries of evoked responses, such as the first, about 50 to 200, evoked responses in a series of about 500 to 2000 consecutive sound stimulus.

Alternatively and/or additionally, in some examples, the latency variation may be calculated using only an evoked response of at least one neuron from one stimulus. An average value is calculating for the response within a window to which subpart of the evoked response is compared. This will give a measure of how much the curve swing and/or shift.

Figure 3B:
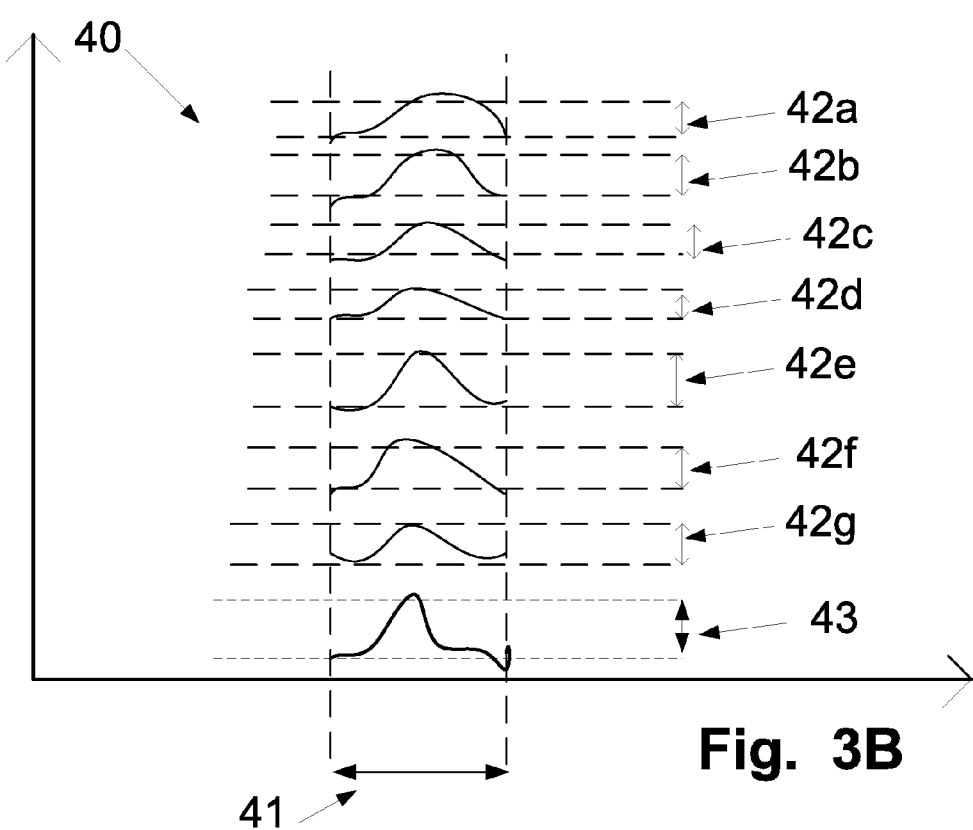
FIG. 3B is illustrating a graph for illustrating a principle of determining cellular amplitude variance and/or volatility of one neuron's evoked response in a window having a time width.

FIG. 3B, shows a graph 40 for illustrating a principle of determining cellular amplitude variance and/or volatility of at least one neuron's evoked response in a window having a time width 41. The width of the window may be in the range 1 to 4 ms, preferably around 2.5 ms. The width of the window has to be large enough to cover a sufficient area of a selected at least one neuron's evoked response. The area of the window should preferably not overlap with neighbouring neurons' response areas. The cellular amplitude variance and/or volatility are a measure of uncertainty in the selected neuron cells. Peak 43 illustrates a determined average amplitude from a number of evoked responses of at least one neuron, such as a group of neurons belonging to the same cluster or structure. By comparing the amplitude of each peak 42a-42h with the amplitude of the average evoked response of peak 43, the variance and/or volatility for each evoked response may be calculated with respect to the amplitude. The average may be calculated by using all the evoked responses from a series of sound stimulus.

Alternatively, for example when doing real-time evaluations, the average amplitude may be calculated from a first subseries of evoked responses, such as the first, about 50 to 200, evoked responses in a series of about 500 to 2000 consecutive sound stimulus.

Alternatively and/or additionally, in some examples, the amplitude variation may be calculated using only an evoked response from one stimulus. An average value is calculating for the response within a window to which subpart of the evoked response is compared. This will give a measure of how much the curve swing and/or shift.

Figure 4A:
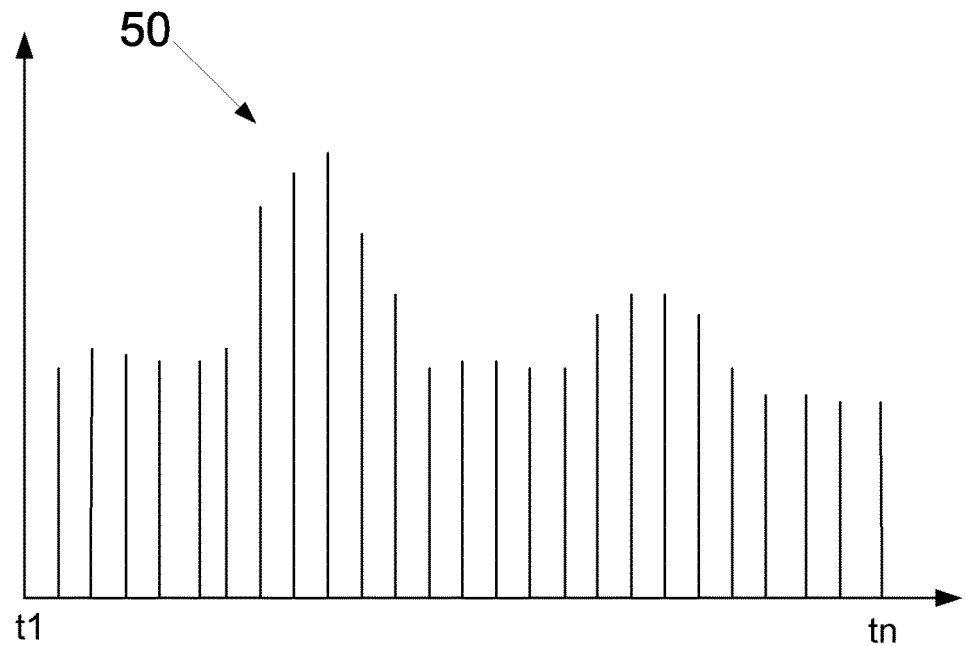
FIGS. 4A and 4B are illustrating graphs for illustrative purpose of a determined cellular latency or amplitude variance and/or volatility of one neuron's evoked response in a window having a time width.

FIG. 4A, is illustrating a graph 50 for illustrative purpose of a determined cellular latency or amplitude variance and/or volatility of at least one neuron's evoked response in a window having a time width. From a set of recorded evoked responses from at least one neuron, both a plot illustrating cellular latency variance and/or volatility and one plot showing cellular amplitude variance and/or volatility may be obtained. Each line in the graph 50 illustrates the variance in an evoked neuron's response as a response to one presented sound stimulus to a subject. The higher a line is in the graph, the higher the variance for that specific evoked response as a result of a single stimulus. In the illustrative graph 50 t1 is marking the start of the test and to is a later arbitrary time.

Figure 4B:
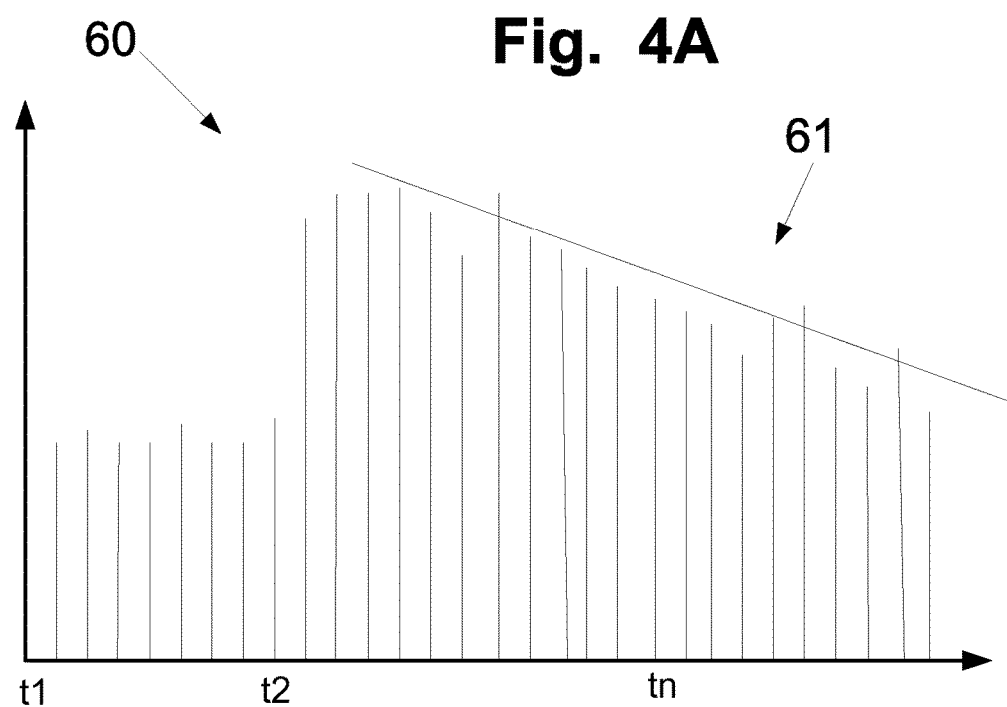

FIG. 4B, is illustrating a graph 60 for illustrative purpose similar to the graph 50 in FIG. 4A. In this graph t1 illustrates the start of the test of a subject. At t2 the subject is delivered a psychoactive, chemical or herbal compound or substance which may have an effect on the variance and/or volatility of a selected at least one neuron's evoked response, here illustrated as an increase in the variance and/or volatility. The effect may then decline. The trend-line 61 may be used to determine the habituation which may be used as a measure of the behavior in the variance of the selected at least one neuron.

Additionally, in some examples, these measurements may be conducted in real-time. This may be done by only calculating an average using the responses between t1 and t2 when the subject is under no influence of a psychoactive, chemical or herbal compound or substance. The average is calculated at t2. After the time t2, when the subject has been delivered a psychoactive, chemical or herbal compound or substance, the calculated average between t1 and t2 may be used to in real-time determining the variance and/or volatility after the time t2.

Figure 5:
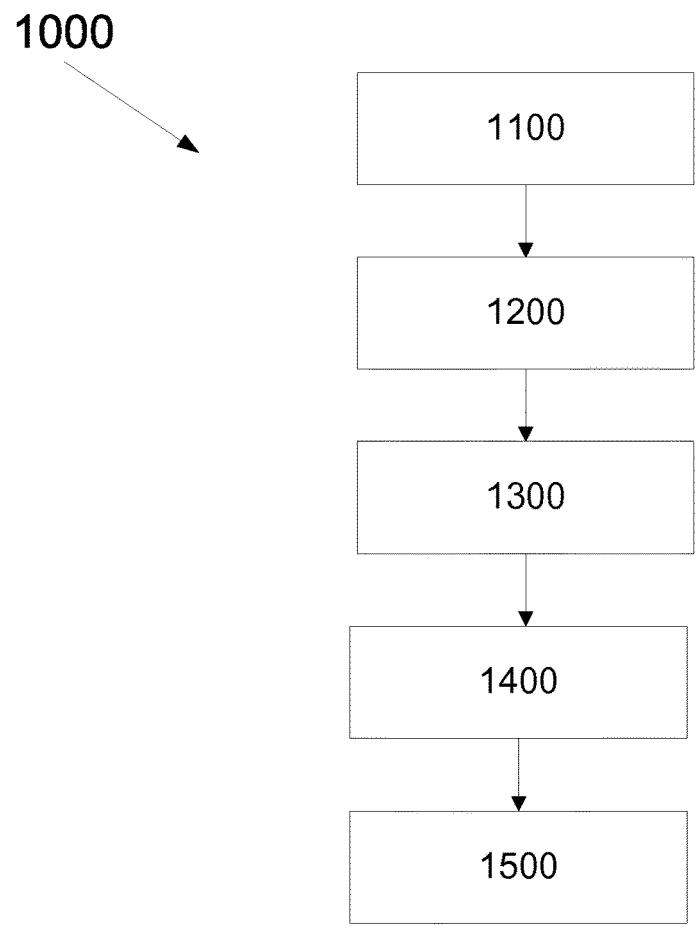
FIG. 5 is illustrating a schematic illustration of a method for detecting a brain response state of a subject.

FIG. 5, is schematically illustrating a method 1000 for detecting a brain response state of a subject, preferably a brainstem response. The detection is performed by determining cellular variance and/or volatility of at least one neuron's evoked response.

A stimuli generator is repeatedly presenting 1100 the subject with a sound stimulus for evoking a brain response. A detection unit is detecting 1200 the evoked brain response signal related to each of the presented sound stimulus.

Determining 1300 a window having a time width covering at least partly an area of the selected at least one neuron's evoked response is performed. The time width of the window may be determined either automatically or having a predetermined time width.

A control unit is then first calculating 1400 an average response signal over the determined window. Then the control unit may determining 1500 the cellular variance and/or volatility in the area of the selected at least one neuron's evoked response by comparing with the average response signal.

Figure 6A:
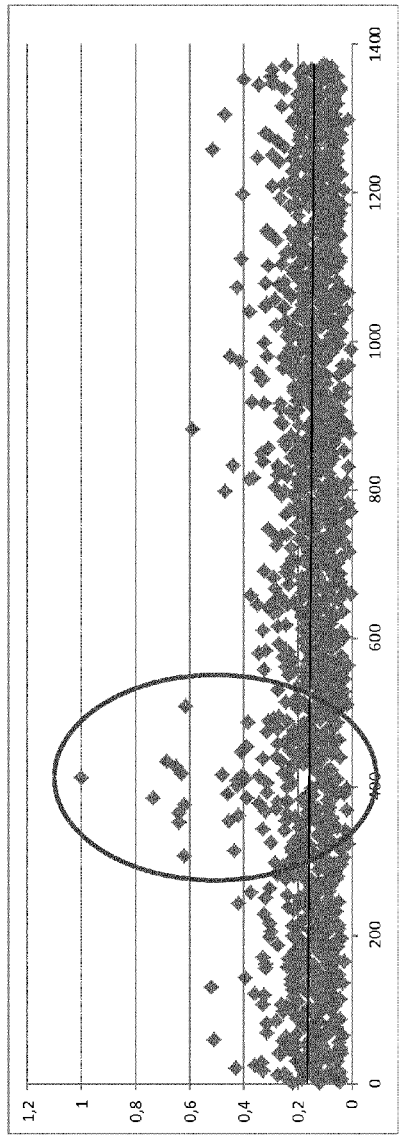
FIGS. 6A and 6B are illustrating an example of measurements performed on one reference subject (FIG. 6A) and one subject diagnosed with ADHD (FIG. 6B), the selected area of the response signal is the pons area.
Figure 6B:
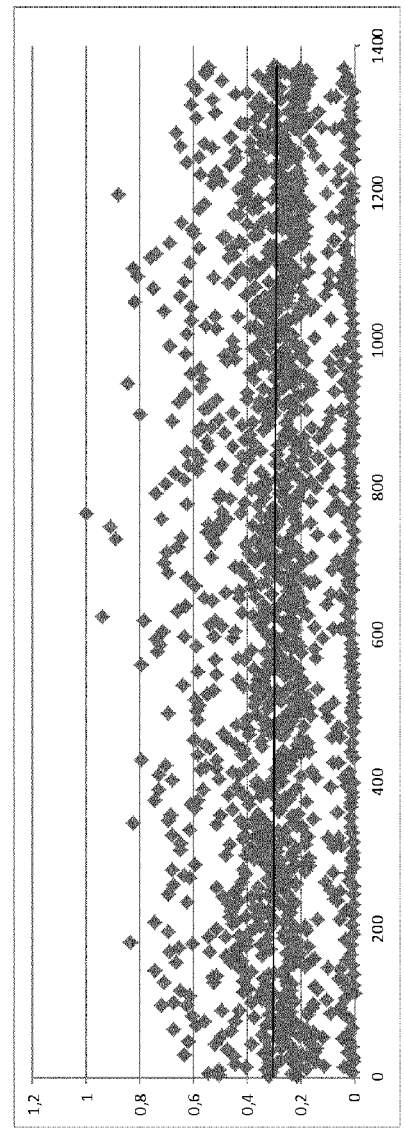

FIGS. 6A and 6B, are illustrating an examples of measurements performed on one reference subject and one subject diagnosed with ADHD. The test subjects are two men both born 1988.

In the graph 70 in FIG. 6A, the values of the reference subject is plotted. The measurement was performed using 1400 sound stimuli and a time window of 2.5 ms, covering the evoked response in pons. On the Y axis the Microvolt of the cellular amplitude variance values in pons are plotted. The circle is highlighting an increase in the variance around 300 sound stimuli, which is a normal reaction.

In the graph 80 in FIG. 6B, the values of the subject diagnosed with ADHD is plotted. The measurement was performed using 1400 sound stimuli and a time window of 2.5 ms, covering the evoked response in pons. On the Y axis the Microvolt of the cellular amplitude variance values in pons are plotted. The overall enlargement of the variance and the lack of the normal increase of variance around 300, as for a normal person, may be traits of ADHA.

The k-values of the trend-line may be calculated being −2,075 for the reference subject and −1,081 for the subject diagnosed with ADHD. The k-value implies that the habituation, as revealed by all analysis, is altered in ADHD. The ADHD group has half the habituation effect as compared to healthy reference controls.

FIGS. 7A and 7B, are illustrating an examples of measurements performed on one reference subject and one subject diagnosed with ADHD. The test subjects are two men both born 1988, same subjects as in FIGS. 6A and B.

In the graph 90 in FIG. 7A, the values of the reference subject is plotted. The measurement was again performed using 1400 sound stimuli and a time window of 2.5 ms, covering the evoked response in thalamus. On the Y axis the Microvolt of the cellular amplitude variance values in thalamus are plotted. The circle is highlighting an increase in the variance around 300 sound stimuli, which is a normal reaction.

In the graph 100 in FIG. 7B, the values of the subject diagnosed with ADHD is plotted. The measurement was performed using 1400 sound stimuli and a time window of 2.5 ms, covering the evoked response in thalamus. On the Y axis the Microvolt of the cellular amplitude variance values in thalamus are plotted. The overall enlargement of the variance and the lack of the normal increase of variance around 300, as for a normal person, may be traits of ADHA.

The k-values of the trend-line may be calculated, in this case being −2,159 for the reference subject and −1,181 for the subject diagnosed with ADHD. The calculated k-values imply that the habituation, as revealed by all analysis, is altered in ADHD. The ADHD group has half the habituation effect as compared to healthy reference controls.

In FIGS. 6A and 6B as well as in FIGS. 7A and 7B, the variance inclination from first clicks to last is reduced in ADHD, which implying that these deficiencies could be traits for ADHD. A method and device for making such computations would be very useful for a fast assessment of patient states. Further and increased accuracy in providing a diagnosis may be achieved. The method and device may perform a complete recording of information from a subject and analyzing the information to determining the variance over time in a couple of minutes. Thus the method and system may quickly detect abnormalities, as demonstrated for ADHD in the above examples.

Figure 8A:
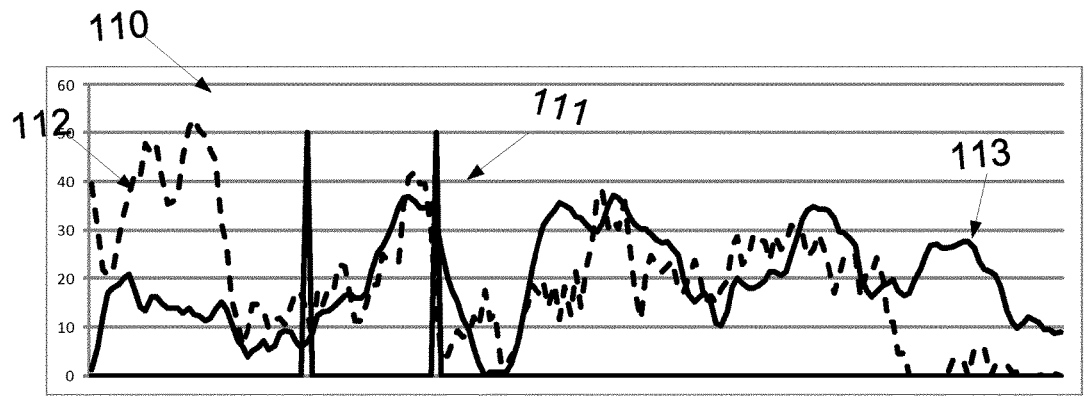
FIG. 8A to 8C are depicting an example of classic auditory brainstem response measurements by using averaging of a reference subject and a subject diagnosed with ADHD, the used area is pons.
Figure 8B:
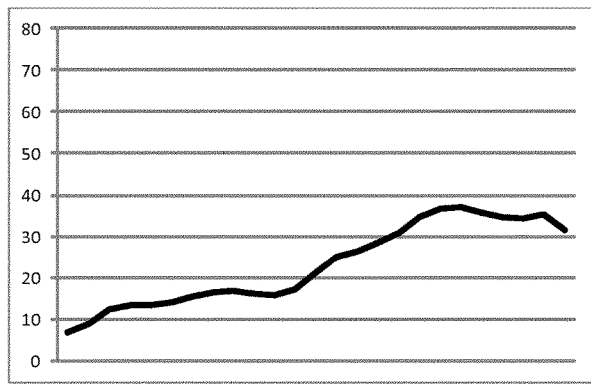
Figure 8C:
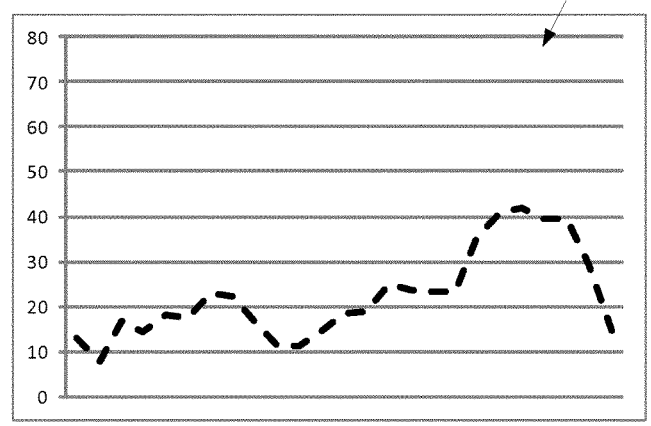

FIG. 8A to 8C, are illustrating an example of an old standard evaluation.

FIG. 8A is depicting an example of a full averaged ABR output 110 from a classic ABR measurement. The average is made from a number of evoked responses. The range of the total spectra of responses is from 0 to 10 ms. The Dashed line 112 is a normal reference subject while the solid line 113 is a subject diagnosed with ADHD. The two peaks 111 show the pons area and a time width of about 2 ms.

FIG. 8B is depicting a zoomed in activity 120 of the subject diagnosed with ADHD. The variance within this area is established to 100.

FIG. 8C is depicting a zoomed in activity 130 of the reference subject not diagnosed with ADHD. The variance within this area is established to 100.

For both subjects there is variance of 100 within the area. Thus it may be concluded that when averaging there is no difference in variance between a subject with ADHD and a reference subject.

Figure 9B:
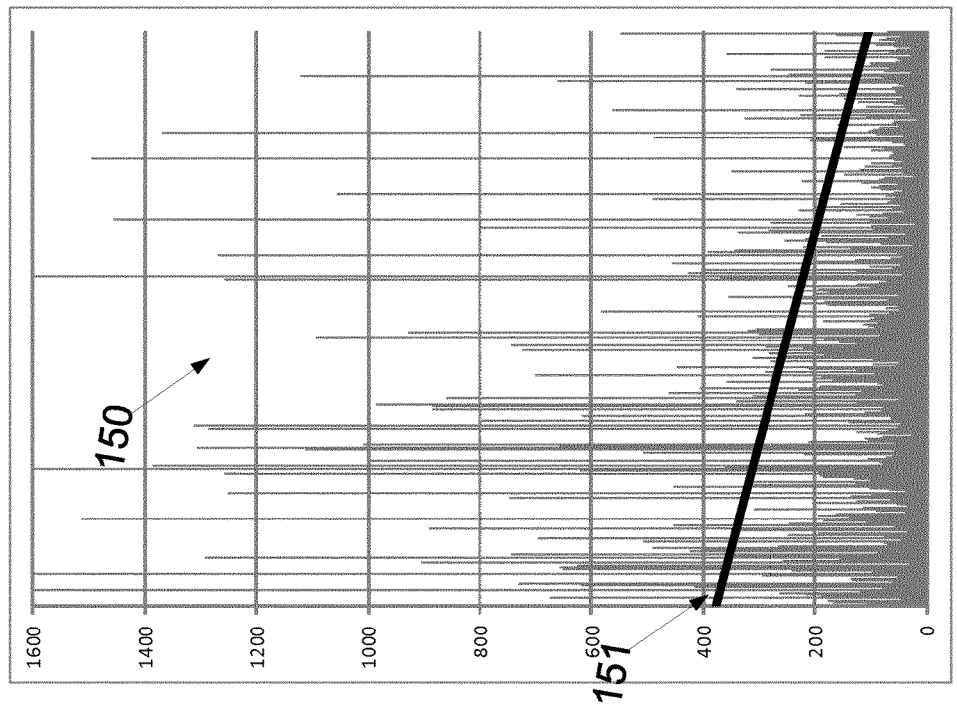
FIGS. 9A and 9B are illustrating an example of the advantages of using variance of each individual response rather than averaging. The used data is same as in the example of FIG. 8A to 8C.
Figure 9A:
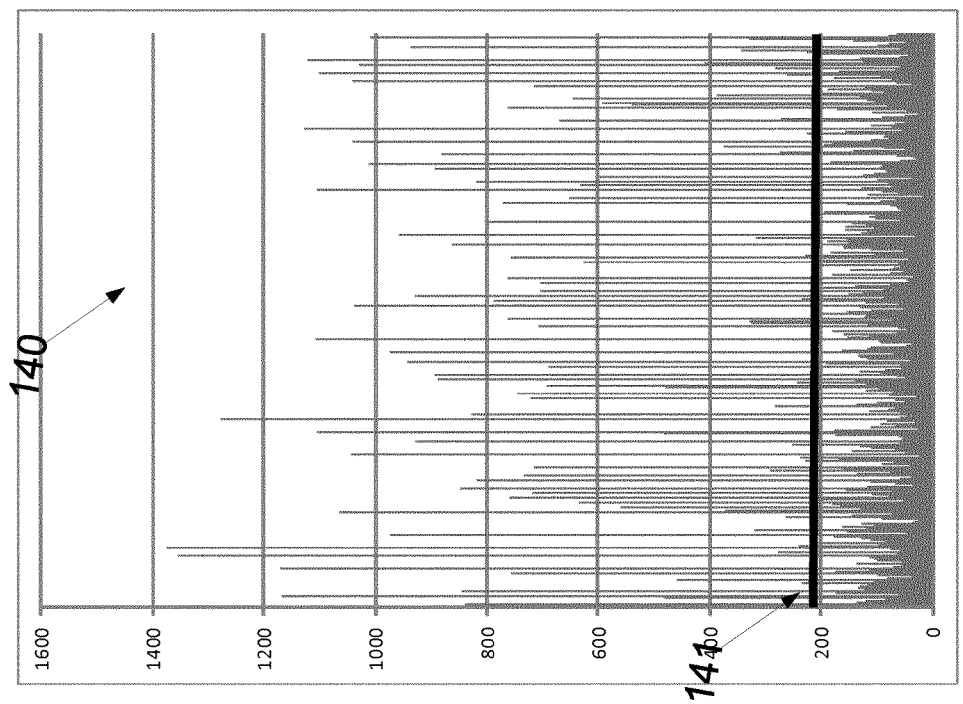

FIG. 9A and FIG. 9B are examples of using variance of each individual response. The data is the same as for averaging example of FIG. 8A to 8C. The area showed is again the pons area using a 2 ms time width of the window. The numbers of evoked responses are 500 illustrated by lines.

FIG. 9A is depicting the variance plot 140 of the subject diagnosed with ADHD. To increase the clarity, the trend-line 141 is plotted. As in the example of 6A and 6B, there is no revealed habituation for the ADHD subject by this method. Thus it is very clear that a non-changing variance characterize the ADHD subject.

FIG. 9B is depicting the variance plot 150 of the non-ADHD reference subject. To increase the clarity, the trend-line 151 is plotted. As in the example of 6A and 6B, there is a habituation for the reference subject shown by this method. Thus it is very clear that a change in variance characterize the non-ADHD reference subject.

These examples given illustrate the improvement over the old averaging method as well as the increase in possibilities of a fast assessment and diagnosis of a subject. The need of using normalised databases with healthy subjects for the assessment, as for the old averaging method, may for the variance method be redundant since the information may directly obtained from the variance and/or volatility determination.

The present disclosure has been described above with reference to specific examples. However, other examples than the above described are equally possible within the scope of the disclosure. Different method steps than those described above, performing the method by hardware or software, may be provided within the scope of the disclosure. The different features and steps of the disclosure may be combined in other combinations than those described. The scope of the disclosure is only limited by the appended patent claims.

The invention claimed is:

1. A method for detecting a brain response state of a subject, said method comprising:
repeatedly presenting a sound stimulus to a subject;
detecting evoked brainstem response signals during said repeatedly presenting said sound stimulus and storing said detected evoked brainstem response signals on a brainstem information storage device; wherein each of said evoked brainstem response signals is an electrophysiological signal comprising at least one peak from at least one neuron related to each of said sound stimulus;

displaying using a computer a brainstem response display showing an average evoked response signal within a predetermined time window; said average evoked response signal being calculated based on said evoked brainstem response signals occurring during said predetermined time window;

displaying using said computer in said brainstem response display either 1) each of said evoked brainstem response signals occurring during said predetermined time window, or 2) subparts of said evoked brainstem response signals occurring during said predetermined time window;

wherein said evoked brainstem response signals or said subparts of said evoked brainstem response signals are positioned in said brainstem response display to show a variance relative to said average evoked response signal.

2. The method for detecting a brain response state of claim 1, wherein said evoked brainstem response signals or said subparts of said evoked brainstem response signals are aligned with said averaged evoked response signal so as to display said variance.

3. The method for detecting a brain response state of claim 1, wherein said variance is displayed as a difference in amplitude of said evoked brainstem response signals or said subparts of said evoked brainstem response signals and said averaged evoked response signal.

4. The method for detecting a brain response state of claim 1, wherein said variance is displayed as a difference in latency of said evoked brainstem response signals or said subparts of said evoked brainstem response signals and said averaged evoked response signal.

5. The method for detecting a brain response state of claim 1, wherein said average evoked response signal is calculated by said computer based on a subseries of said evoked brainstem response signals.

6. The method for detecting a brain response state of claim 1, wherein said sound stimulus comprises a first consecutive train of modified sound pulses and a second consecutive train of modified sound pulses.

7. A device for detecting a brain response state of a subject, comprising:
a sound stimuli generating unit configured to repeatedly generate a sound stimulus to said subject;
a detection electrode configured to detect evoked brainstem response signals while said sound stimuli generating unit generates said sound stimulus; wherein each of said evoked brainstem response signals is an electrophysiological signal comprising at least one peak from at least one neuron related to each of said sound stimulus;
a brainstem information storage device configured to receive and store said evoked brainstem response signals; and,
a computer executing software that calculates an average evoked response signal over a predetermined length of time; said average evoked response signal comprising either 1) an average of said evoked brainstem response signals during said predetermined length of time; or 2) based on one of said evoked brainstem response signals during said predetermined length of time;
wherein said software displays on said computer said average evoked response signal during said predetermined length of time, and either 1) each of said evoked brainstem response signals occurring during said predetermined time window, or 2) subparts of said evoked brainstem response signals occurring during said predetermined time window;
wherein said evoked brainstem response signals or said subparts of said evoked brainstem response signals are positioned on said computer to show a variance relative to said average evoked response signal.

8. The device of claim 7, wherein said evoked brainstem response signals or said subparts of said evoked brainstem response signals are aligned with said averaged evoked response signal so as to display said variance.

9. The device of claim 7, wherein said variance is displayed as a difference in amplitude of said evoked brainstem response signals or said subparts of said evoked brainstem response signals and said averaged evoked response signal.

10. The device of claim 7, wherein said variance is displayed as a difference in latency of said evoked brainstem response signals or said subparts of said evoked brainstem response signals and said averaged evoked response signal.

11. The device of claim 7, wherein said average evoked response signal is calculated by said computer based on a subseries of said evoked brainstem response signals.

12. The device of claim 7, wherein said sound stimulus comprises a first consecutive train of modified sound pulses and a second consecutive train of modified sound pulses.

13. A method for detecting a brain response state of a subject, said method comprising:
repeatedly presenting a sound stimulus to a subject;
detecting evoked brainstem response signals during said repeatedly presenting said sound stimulus and storing said detected evoked brainstem response signals on a brainstem information storage device; wherein each of said evoked brainstem response signals is an electrophysiological signal comprising at least one peak from at least one neuron related to each of said sound stimulus;
calculating using a computer an average evoked response signal within a predetermined time window; said average evoked response signal being calculated based on said evoked brainstem response signals occurring during said predetermined time window;
displaying using said computer a plurality of variance levels at positions along said predetermined time window; said plurality of variance levels calculated by said computer by determined a difference between said average evoked response signal and either 1) each of said evoked brainstem response signals occurring during said predetermined time window, or 2) subparts of said evoked brainstem response signals occurring during said predetermined time window.

14. The method for detecting a brain response state of claim 13, wherein said evoked brainstem response signals or said subparts of said evoked brainstem response signals are aligned with said averaged evoked response signal so as to display said variance.

15. The method for detecting a brain response state of claim 13, wherein said variance is displayed as a difference in amplitude of said evoked brainstem response signals or said subparts of said evoked brainstem response signals and said averaged evoked response signal.

16. The method for detecting a brain response state of claim 13, wherein said variance is displayed as a difference in latency of said evoked brainstem response signals or said subparts of said evoked brainstem response signals and said averaged evoked response signal.

17. The method for detecting a brain response state of claim 13, wherein said average evoked response signal is calculated by said computer based on a subseries of said evoked brainstem response signals.

18. The method for detecting a brain response state of claim 13, wherein said sound stimulus comprises a first consecutive train of modified sound pulses and a second consecutive train of modified sound pulses.

\* \* \* \* \*